US006287833B1

(12) United States Patent
Miyada et al.

(10) Patent No.: US 6,287,833 B1
(45) Date of Patent: Sep. 11, 2001

(54) METHOD FOR DETECTING CANDIDA INFECTION

(75) Inventors: Charles Garrett Miyada, Mountain View; Arthur C. Switchenko, Palo Alto; Melanie W. Quong, La Jolla; Man-Ying Laurie Wong, Fremont, all of CA (US)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/472,599

(22) Filed: Jun. 7, 1995

Related U.S. Application Data

(62) Division of application No. 08/400,417, filed on Mar. 3, 1995, now Pat. No. 5,451,517, which is a continuation of application No. 08/184,764, filed on Jan. 21, 1994, now abandoned, which is a continuation of application No. 07/731,218, filed on Jul. 12, 1991, now abandoned.

(51) Int. Cl.$^7$ ..................................................... C12N 9/04
(52) U.S. Cl. ...................... 435/190; 435/189; 435/255.4
(58) Field of Search .................................... 435/190, 189, 435/255.4, 921, 922, 923, 924

(56) References Cited

U.S. PATENT DOCUMENTS 5,126,266   6/1992   Jeffries et al. .................... 455/255

OTHER PUBLICATIONS

Soyama and Ono, *Clinica Chimica Acta*, 1987, vol. 168, pp 259–260.
Neuberger, et al., *Biochem. J.*, 1979, vol. 183, pp 31–42.
Kiehn, et al., *Science*, Nov. 1979, vol. 206, pp 577–580.
Bernard, et al., *J. Infect. Diseases*, Apr. 1985, vol. 151(4), pp 711–715.
Wong and Brauer, *J. Clin. Microbiol*, Sep. 1988, vol. 26(9), pp 1670–1674.
Wong and Castellanos, *J. Chromatography*, 1989, vol. 495, pp 21–30.
Roboz, et al., *J. Chromatography*, 1990, vol. 500, pp 413–426.
Jones, *Clin. Microbiol. Reviews*, Jan. 1990, vol. 3, pp 32–45.
Ness, et al., *J. of Infectious Diseases*, Mar. 1989, vol. 159(3), pp 495–502.
Cabezudo, et al., *Eur. J. Clin. Microbiol. Infect. Dis.*, Sep. 1989, vol. 8(9), pp 770–777.
Walsh, et al., *New England J. Medicine*, Apr. 1991, vol. 324(15), pp. 1026–1031.
Minamide, et al., *Bull. Univ. Osaka Prefect. Ser. B*, 1987, vol. 39, pp 1–7.
Ohmono, et al., *J. Ferment. Technol.*, 1983, vol. 61(4), pp 373–378.
Wu, J., *Gen. Microbiol.*, 1976, vol. 94(2), pp 246–256.
Szumilo, et al., *Acta Microbiol. Pol.*, 1980, vol. 29(3), pp 233–248.
Fossitt, et al., *Methods Enzymol.*, 1966, vol. 9, pp 180–186.
Ingram, et al., *Methods Enzymol.*, 1966, vol, 9, pp 186–188.
Primrose, et al., *J. Bacteriol.*, 1980, vol. 141(3), pp 1109–1114.
Kyslik, et al., *Biotechnol Lett.*, 1984, vol. 6(1), pp 25–30.
Scangos, et al., *J. Bacteriol.*, 1978, vol. 134(2), pp 492–500.
Neal, et al., *J. Bacteriol.*, 1970, vol. 101(3), pp 910–915.
Chartnetzky, et al., *J. Bact.*, 1974, vol. 119(1), pp 170–175.
Shakhova, *Biol. Nauki*, 1975, vol. 18(8), pp 89–91.
Martinez de Drets, et al., *J. Bacteriol.*, 1970, vol. 103(1), pp 97–103.
Charnetzky, et al., *J. Bact.*, 1974 vol., 119(1), pp 176–182.
Moran, et al., *J. Bacteriol.*, 1979, vol. 138(3), pp 823–831.
Scangos, et al., *J. Mol. Evol.*, 1979, vol. 12(3), pp 189–205.
Sikyta, et al., *Microbiol. Sci.*, 1985, vol. 2(1), pp 25–27.
Speth, et al., *Abstr. Annu. Meet. Am. Soc. Microbiol.*, 1974, vol. 74, p 156.
Wong, et al., *Abstract Gen. Meet. America Society for Microbiology*, Washington D.C., "Isolation of the D-arabinitol dehydrogenase gene of *Candida Albicans*," Abstract F–75May 5, 1991, vol. 91, p 421.

*Primary Examiner*—Leon B. Lankford, Jr.
(74) *Attorney, Agent, or Firm*—Theodore J Leitereg

(57) ABSTRACT

A D-arabinitol dehydrogenase enzyme is disclosed. The enzyme is capable of catalyzing the oxidation of D-arabinitol and substantially incapable of catalyzing the oxidation of D-mannitol and is substantially free of other enzymes capable of oxidizing D-mannitol. Also disclosed are methods for determining D-arabinitol. In one embodiment the method comprises the steps of providing in combination (1) a medium suspected of containing D-arabinitol and (2) a D-arabinitol dehydrogenase enzyme and examining the medium for the product of the oxidation of the D-arabinitol. The enzyme utilized is capable of catalyzing the oxidation of D-arabinitol and substantially incapable of catalyzing the oxidation of D-mannitol. Kits for conducting the present method are also disclosed.

7 Claims, No Drawings

METHOD FOR DETECTING CANDIDA INFECTION

This is a Division of application Ser. No. 08/400,417, filed Mar. 3, 1995, now U.S. Pat. No. 5,451,517, which is a File Wrapper Continuation of application Ser. No. 08/184,764, filed Jan. 21, 1994, now abandoned, which is a File Wrapper Continuation of application Ser. No. 07/731,218, filed Jul. 12, 1991, now abandoned, the disclosures of which are incorporated herein by reference.

BACKGROUND OF THE INVENTION

1. Field of the Invention

At present the laboratory tools available to clinicians for the diagnosis of invasive candidiasis are limited. Surveillance cultures of peripheral sites have little predictive value, with the possible exception of Candida tropicalis infection in neutropenic patients. Blood cultures, even when they are tailored for optimal growth of fungi, are slow, insensitive, and nonspecific. Measurement of antibodies to Candida is not helpful in immunosuppressed patients who comprise the very group that is most vulnerable to invasive infections. Detection of circulating fungal products, particularly mannan, provides the desired level of specificity, but the clinical sensitivity of current assays is disappointing, and the technology for performing them is not readily portable to clinical laboratories. Commercially available latex agglutination kits detect uncharacterized antigen(s) and lack sensitivity and specificity.

Most medically important species of Candida produce micromolar amounts of the pentitol D-arabinitol in vitro and there is considerable evidence that patients with invasive candidiasis have higher serum D-arabinitol levels and higher serum D-arabinitol/creatinine ratios than uninfected patients. Therefore, D-arabinitol is potentially useful as a diagnostic marker for invasive candidiasis, a disease that often is difficult to diagnose antemortem by traditional methods.

Enantioselective measurements of D-arabinitol in human serum were originally made by combined microbiologic-gas chromatographic (GC) and enzymatic-GC techniques. These approaches were, however, time consuming and cumbersome. Recently, two GC methods have been developed that employ columns with a chiral stationary phase capable of separating enantiomers of arabinitol. Although these methods are highly specific for D-arabinitol and do not require serum pretreatment by enzymatic or microbiologic techniques, they are too cumbersome for routine use in the clinical laboratory. A more practical enzymatic fluorometric method has been developed that uses an *Enterobacter aerogenes* (*Klebsiella Pneumoniae*) D-arabinitol dehydrogenase. Unfortunately, cross reactivity of the dehydrogenase with D-mannitol, a hexitol normally present in human serum, reduces the specificity of this assay.

2. Description of the Related Art

Soyama and Ono, in *Clinica Chimica Acta*, 149 (1985) 149–154, describe an enzymatic fluorometric method for the determination of D-arabinitol in serum by initial rate analysis.

Soyama and Ono describe an improved procedure for determining serum D-arabinitol by a resazurin-coupled enzymatic method in *Clinica Chimica Acta*, 168 (1987) 259–260.

The purification and properties of *Klebsiella aerogenes* D-arabinitol dehydrogenase are discussed by Neuberger, et al., in *Biochem. J.*, 183 (1979) 31–42.

Kiehn, et al., in *Science*, 206 (1979) 577–580, describe a gas-liquid chromatographic method for measuring D-arabinitol in human serum and assess the clinical usefulness of this method for detecting candidiasis. In actuality, total pentitol (D- and L-arabinitol, xylitol and ribitol) concentration is being measured by this method.

Bernard, et al., in *J. Infect. Dis.*, 151(4)(1985) 711–715, describe a combined microbiologic-GC method for determining the stereoisomeric configuration of arabinitol in serum, urine, and tissues in invasive candidiasis. In this method, D-arabinitol concentrations are calculated as the difference between serum arabinitol levels determined by GC before and after sample incubation with a strain of *C. tropicalis*, which consumes D-arabinitol once preferred substances are exhausted. Unfortunately, the method requires a 24-hour incubation step, is susceptible to interference by anti-fungal drugs, and is insufficiently sensitive.

Wong and Brauer, in *J. Clin. Microbiol.* 26 (1988) 1670–1674, describe a combined enzymatic-GC method for the enantioselective measurement of D-arabinitol in human serum. In this method, D-arabinitol dehydrogenase from *K. pneumoniae* is used instead of *C. tropicalis* cells for the removal of D-arabinitol from serum; and D-arabinitol levels are calculated as the difference between arabinitol levels determined by GC in the untreated and enzyme-treated serum. Although this combined enzymatic-GC method is unaffected by antifungal drugs, sufficiently sensitive to quantify D-arabinitol in most serum specimens, and can be completed within a few hours, the technique requires that each specimen be analyzed twice by GC to determine the concentration of D-arabinitol.

Enantioselective measurement of the Candida metabolite D-arabinitol in human serum using multidimensional gas chromatography and a new chiral stationary phase is disclosed by Wong and Castellanos, in *J. Chromatography*, 495 (1989) 21–30. This technique is sensitive and highly specific for D-arabinitol, but requires that each specimen be fractioned successively over GC columns containing a conventional and chiral stationary phase.

The separation and quantification by gas chromatography-mass spectrometry of arabinitol enantiomers to aid the differential diagnosis of disseminated candidiasis is disclosed by Roboz, et al., in *J. Chromatog.*, 500 (1990) 413–426. The columns used in this approach have a limited useful lifetime and the procedure is laborious and time-consuming.

A review of techniques for the diagnosis of invasive candidiasis is described by Jones in *Clin. Microbiol. Rev.*, 3 (1990) 32–45.

Ness, et al., in *The Journal of Infectious Diseases*, 159 (1989) 495–502 describe the Candida antigen latex test for detection of invasive candidiasis in immunocompromised patients.

Cabezudo, et al., discuss the value of the Cand-Tec Candida antigen assay in the diagnosis and therapy of systemic candidiasis in high-risk patients (*Eur. J. Clin. Microbiol. Infect. Dis.*, 8 (1989) 770–777).

Walsh, et al., in *N. Engl. J. Med.*, 324(15) (1991) 1026–1031, assess the clinical utility of the Candida enolase antigen test for detecting candidiasis in cancer patients.

SUMMARY OF THE INVENTION

One embodiment of the present invention is directed to an enzyme in purified form specific for D-arabinitol.

Another embodiment of the present invention is directed to a D-arabinitol dehydrogenase enzyme capable of catalyzing the oxidation of D-arabinitol and substantially incapable of catalyzing the oxidation of D-mannitol and that is substantially free of other enzymes capable of oxidizing D-mannitol.

Another embodiment of the present invention is a method for determining D-arabinitol. The method comprises the steps of providing in combination (1) a medium suspected of containing D-arabinitol and (2) a D-arabinitol dehydrogenase enzyme and examining the medium for the product produced as a result of the oxidation of the D-arabinitol. The enzyme utilized is capable of catalyzing the oxidation of D-arabinitol and substantially incapable of catalyzing the oxidation of D-mannitol.

Another aspect of the invention is a method for detecting the presence of a Candida organism in a host. The method comprises the step of examining a sample from the host for the presence of D-arabinitol utilizing a D-arabinitol dehydrogenase enzyme. The enzyme is capable of utilizing D-arabinitol as a substrate and substantially incapable of utilizing D-mannitol as a substrate.

Another embodiment of the invention concerns a method of detecting a Candida infection in a patient. The method comprises the steps of providing in combination a sample from the patient, a D-arabinitol dehydrogenase enzyme capable of catalyzing the oxidation of D-arabinitol by nicotinamide adenine dinucleotide (NAD$^+$) and substantially incapable of catalyzing the oxidation of D-mannitol, and examining the combination for the amount of NADH formed in a given time. The term "NAD$^+$" shall mean the natural coenzyme and NAD$^+$ mimetics including NAD$^+$ attached to a support and thio analogs, which contain one or more sulfur atoms in place of one or more oxygen atoms of the NAD$^+$. The amount of NAD$^+$ reduced form (NADH) is used to assist in the clinical diagnosis of a Candida infection.

Another aspect of the present invention involves a composition comprising (1) a D-arabinitol dehydrogenase enzyme capable of utilizing D-arabinitol as a substrate and substantially incapable of utilizing D-mannitol as a substrate and (2) NAD$^+$.

Another embodiment of the present invention concerns a D-arabinitol dehydrogenase enzyme capable of binding to at least one of the monoclonal antibodies selected from the group consisting of 3D6 and 5E11, where the enzyme is substantially free of other enzymes capable of oxidizing D-mannitol.

Another embodiment of the present invention concerns a composition comprising an enzyme where the composition is capable of catalyzing the oxidation of D-arabinitol at a rate at least 20-fold faster than it catalyzes the oxidation of any other naturally occurring polyol.

Another embodiment of the invention is a kit comprising in packaged combination (1) a D-arabinitol dehydrogenase enzyme preparation substantially incapable of catalyzing the oxidation of D-mannitol and (2) NAD$^+$.

Description Of The Specific Embodiments

The present invention is directed to an enzymatic D-arabinitol assay utilizing a particular D-arabinitol dehydrogenase enzyme. The present assay can be performed in much shorter times than known assays and permits following the course of anti-fungal treatment of a Candida infection. Thus, the present invention provides for the detection of a Candida infection based on the determination of D-arabinitol usually in serum or urine. The particular D-arabinitol dehydrogenase enzyme employed permits the discrimination between D-arabinitol and other metabolites such as D-mannitol.

The D-arabinitol dehydrogenase (DADH) enzyme employed is capable of catalyzing the oxidation of D-arabinitol and substantially incapable of catalyzing the oxidation of D-mannitol and is substantially free of other enzymes capable of oxidizing D-mannitol. DADH is an enzyme having the I.U.B. classification of oxidoreductase acting on the CH—OH group of donors having D-arabinitol as a substrate.

The term "capable of catalyzing the oxidation of D-arabinitol" means that the pure DADH has a specific activity for catalysis of the oxidation of D-arabinitol of at least 50 international units (IU)/mg, preferably at least 100 IU/mg, more preferably at least 150 IU/mg.

The term "substantially incapable of catalyzing the oxidation of D-mannitol" means that the DADH used in the assay has a specific activity for catalysis of the oxidation of D-mannitol less than 1%, preferably less than 0.2%, more preferably less than 0.1% of the specific activity for catalysis of the oxidation of D-arabinitol.

The term "substantially free of other enzymes capable of oxidizing D-mannitol" means that any other enzyme present as an impurity of the DADH is substantially incapable of catalyzing the oxidation of D-mannitol.

The term "specific DADH" means DADH that is substantially incapable of catalyzing the oxidation of D-mannitol and is substantially free of other enzymes capable of oxidizing D-mannitol.

The term "DADH in purified form" means a DADH having a purity of greater than 80%, preferably greater than 90%, more preferably greater than 95%, as determined by sodium dodecylsulfate (SDS) polyacrylamide gel electrophoresis (PAGE). Upon purification of DADH, the DADH in purified form will catalyze the oxidation of other polyols commonly found in human serum at a rate at least 10-fold less than that for D-arabinitol, preferably at least 20-fold less.

The DADH of the present invention can be obtained in a number of ways. For example, the DADH of the invention can be isolated from certain members of the genus Candida. The enzyme is preferably obtained from *Candida tropicalis* and *Candida shehatae*. DADH enzyme from other species can be identified by determining whether the DADH enzyme can bind to at least one of the monoclonal antibodies to the DADH from *Candida tropicalis* selected from the group consisting of 3D6 and 5E11. These monoclonal antibodies are prepared by standard hybrid cell technology and are described herein.

An example, by way of illustration and not limitation, of a purification protocol for DADH from *Candida tropicalis* is as follows: The cells utilized for obtaining the enzyme of the present invention are preferably cultivated in a liquid nutrient medium that contains D-arabinitol as a carbon source as well as nitrogen, vitamins and trace metals. The cells are grown to late log phase at room temperature on a gyrotary shaker. The cells are then harvested, washed, pelleted and resuspended in a suitable buffer containing the appropriate proteinase inhibitors. The cells are then disrupted. Yeast cells are usually subjected to mechanical breakage such as a high speed vibrating bead mill or high pressure shearing, which is accomplished with, for example, a French pressure cell. Bacterial cells may be disrupted enzymatically (e.g., lysozyme), with ultrasound, or by the two methods described above. The resultant cell suspension is then subjected to centrifugation(s) that pellet unbroken cells, cell wall material and possibly membranes and ribosomes. The supernatant is then treated with highly positively charged polymers such as protamine sulfate, which will selectively precipitate nucleic acids and their associated proteins. The enzyme is then precipitated from the solution with a salt (e.g., ammonium sulfate), organic solvent (e.g., acetone), or organic polymer (e.g., polyethylene glycol). Final purification of the enzyme may be carried out using standard techniques such as ion exchange chromatography, reverse-phase chromatography, gel exclusion chromatography, gel electrophoresis, isoelectricfocusing, immunoaffinity chromatography, dye ligand chromatography, and the like.

An enzyme in accordance with the present invention can also be prepared by recombinant DNA technology. Briefly, a gene coding for a DADH enzyme of the invention is obtained, usually by isolation from genetic matter of the organism from which the enzyme was isolated. Generally, the gene is isolated by partial digestion of the DNA followed by centrifugation through a gradient material such as sucrose. Gene fragments are cloned into a suitable cloning vector such as, for example, a plasmid, which is transfected into a host such as, for example, a bacterium, e.g., *Escherichia coli*.

Alternatively, the vector may be other than a plasmid, for example, bacteriophage or cosmid. The particular vector chosen should be compatible with the contemplated host, whether a bacterium such as *E. coli*, yeast, or other cell. The plasmid should have the proper origin of replication for the particular host cell to be employed. Also, the plasmid should impart a phenotypic property that will enable the transformed host cells to be readily identified from cells that do not undergo transformation. Such phenotypic characteristics can include genes providing resistance to growth inhibiting substances, such as an antibiotic. Plasmids are commercially available that encode proteins responsible for resistance to antibiotics, including tetracycline, streptomycin, penicillin and ampicillin. Also required of plasmid vectors are suitable restriction sites that allow the ligation of foreign genes. Similar characteristics will be considered for choosing vectors other than plasmids.

The host cells carrying the gene are selected and gene expression is monitored. If expression is low, the synthesis of DADH in the bacteria may be improved by providing an inducible promoter at the 5'-end of the gene. Such promoters are found in commercially available expression plasmids. Once the gene has been expressed to appropriate levels, the protein is extracted from the bacterium. The DADH enzyme is separated from other proteins by procedures described above. As mentioned above, one way of screening cultures to determine whether a DADH, in accordance with the present invention, is obtained is to utilize a monoclonal antibody that specifically recognizes such DADH. Monoclonal antibodies for this purpose may be synthesized by standard hybrid cell technology based on that reported by Kohler and Milstein in *Nature* 256(1975) 495–497. Briefly, a host is immunized with the specific DADH enzyme isolated as described above from *Candida tropicalis*. The enzyme is injected into the host, usually a mouse or other suitable animal, and after a suitable period of time the spleen cells from the mouse are obtained. Alternatively, unsensitized cells from the host can be isolated and directly sensitized with the DADH enzyme isolate in vitro. Hybrid cells are formed by fusing the above cells with an appropriate myeloma cell line and cultured. The antibodies produced by the cultured hybrid cells are screened for their binding affinity to the DADH enzyme. A number of screening techniques may be employed such as, for example, ELISA screens including forward and reverse ELISA assays. The screening assays can be conducted utilizing DADH enzyme alone or in conjunction with a second enzyme such as, for example, diaphorase, which achieves a reduction in background and an increase in the positive signal.

In the forward assay specific DADH enzyme is provided on a suitable surface such as a microtiter plate. Supernatants from each of the hybrid colonies are individually applied to separate microtiter plate wells. After incubation, the wells are washed and goat antimouse antibodies covalently linked to alkaline phosphatase are added to each of the wells. The wells are again incubated and washed and then filled with a substrate for the phosphatase, such as, for example, p-nitrophenyl phosphate. The wells are then observed for a signal, which indicates the presence of an antibody specific for DADH. Hybrid cells so identified are subjected to recloning.

In the reverse assay the microtiter plate well is coated with rabbit antimouse antibodies. A supernatant from each of the hybrid cell colonies is applied to separate wells. The wells are incubated and washed, and a DADH enzyme preparation is added. $NAD^+$ and D-arabinitol are added to the well. The wells are screened for the reduction of $NAD^+$ to NADH and the hybrid cells of positive wells are selected and recloned to select for the hybrid cells that secrete a homogeneous population of antibodies specific for DADH.

The monoclonal antibodies may also be prepared by cloning and expressing nucleotide sequences or mutagenized versions thereof coding at least for the amino acid sequences required for specific binding of natural antibodies.

Monoclonal antibodies may include a complete immunoglobulin, or fragment thereof, which immunoglobulins include the various classes and isotypes, such as IgA, IgD, IgE, IgGl, IgG2a, IgG2b and IgG3, IgM, etc. Fragments thereof may include Fab, Fv and F(ab')2, Fab', and the like.

As mentioned above, the DADH monoclonal antibodies prepared in accordance with the above may be utilized in assays to screen enzyme preparations isolated from different organisms to obtain and identify the DADH enzyme preparations of the present invention. Particular monoclonal antibodies in accordance with the present invention are those selected from the group consisting of those antibodies recited in Table 2 hereinbelow. Thus, another aspect of the present invention is a DADH enzyme capable of binding to one of the above group of monoclonal antibodies, where the enzyme is substantially free of other enzymes capable of oxidizing D-mannitol.

Another aspect of the present invention involves a method for determining D-arabinitol. The method comprises the steps of providing in combination (1) a medium suspected of containing D-arabinitol, and (2) a specific D-arabinitol dehydrogenase enzyme. The enzyme is capable of catalyzing the oxidation of D-arabinitol and substantially incapable of catalyzing the oxidation of D-mannitol. Many of the DADH enzymes that can be used in the method will be capable of binding to a DADH monoclonal antibody as described above. Generally, the binding of DADH enzyme to the monoclonal antibody will be such that the binding affinity is greater than $10^6$ $M^{-1}$, preferably greater than $10^7$ $M^{-1}$, more preferably greater than $10^8$ $M^{-1}$.

The medium suspected of containing D-arabinitol is generally an aqueous medium which contains a sample from a host. The sample is usually a body fluid. Preferably, the blood of a patient is obtained and the serum fraction is isolated. Alternatively, urine can be used. After an appropriate incubation time, the medium is examined for the product of the oxidation of the D-arabinitol. The amount of D-arabinitol present is determined, usually by reference to a standard curve. The method has application for the detection of the presence of a Candida organism in a host. The presence of Candida is correlated to the amount of D-arabinitol and is usually more closely correlated to the ratio of D-arabinitol to creatinine in the sample. Creatinine is determined by any convenient commercially available method.

A cofactor must be included in the aqueous medium. When present in concentrations in excess of the expected concentration of D-arabinitol, the cofactor serves as the oxidant. Alternatively, it may be present in catalytic concentration, in which case an auxiliary oxidant must be present such as, e.g., pyruvate and lactate dehydrogenase. Usually, the cofactor is $NAD^+$ or a derivative thereof such as $NADP^+$. When the cofactor is in excess of the expected concentration of D-arabinitol, the medium can be examined for the reduced form of the cofactor after the combination is incubated. For $NAD^+$ the reduced form will be NADH. The amount of the reduced cofactor formed in a given time over a predetermined amount is indicative of the amount of D-arabinitol in the sample. The amount of reduced cofactor may be detected directly, e.g., by measuring an amount of fluorescence, or indirectly, e.g., by adding additional reagents.

In one embodiment of the method of the present invention the medium is examined for the amount of the reduced cofactor by adding to the medium a chromophoric reagent that is capable of being reduced by the reduced form of the cofactor. The chromophoric reagent can serve as an auxiliary oxidant and may be present in the medium at the beginning of the incubation period or may be added following incubation. When added following incubation, it will not serve as an auxiliary oxidant. When reduced by the reduced cofactor, the chromophoric reagent will provide a detectible signal. Such chromophoric reagents include, by way of example and not limitation, resazurin, tetrazolium salts such as p-iodophenylnitrophenyltetrazolium, Fem-phenanthroline complex, and the like.

In the embodiment of the present invention utilizing chromophoric reagents, a catalyst that assists in the reduction of the chromophoric reagent by the reduced cofactor is added to the assay medium. The catalyst will usually be capable of being reduced by the reduced cofactor and the reduced form of the catalyst will usually be capable of reducing the chromophoric reagent. Typical catalysts that are useful include diaphorase, phenazine methosulfate, meldola blue, 1-hydroxy-5-alkylphenazinium salts, methylene blue, etc. With NADH and either resazurin or a tetrazolium salt, the enzyme diaphorase is employed as a catalyst.

When a chromophoric reagent is utilized in the method of the present invention, the product is usually detected spectroscopically. For example, the measurement may be made by detection of fluorescence, light absorption, chemiluminescence, light scattering, electroluminescence, etc. Alternatively, the chromophoric reagent need not be converted to a conventional chromophore but is instead converted to a substance that can be detected by nonspectroscopic means such as electrochemical detection.

In a preferred embodiment of the present invention, the assay is carried out in a two-stage incubation in the presence of an amount of $NAD^+$ that will usually be in excess of the highest expected amount of D-arabinitol. The oxidation of D-arabinitol is catalyzed by the DADH enzyme in the initial incubation followed by the catalyzed oxidation of the NADH to $NAD^+$ in the presence of a chromophoric reagent. By adding the catalyst and/or chromophoric reagent following the initial incubation, these reagents can be added in sufficient amounts to cause the reaction with the NADH to occur rapidly and completely. Inclusion of these reagents during the initial incubation also provides useful results, but conversion of the chromophoric reagent to a chromophore by substances in the sample other than D-arabinitol introduces a higher background signal and reduces assay sensitivity.

The method and compositions of the invention may be adapted to most assay formats. The assays may be homogeneous or heterogeneous. In a homogeneous assay approach, the sample may be pretreated if necessary to remove unwanted materials. The reaction usually involves a DADH enzyme and a sample from a patient suspected of a Candida infection. As mentioned above, cofactors, a chromophoric reagent and a catalyst may be included.

The above materials are combined in an aqueous assay medium and the medium is examined for the reduced cofactor. Both the reaction and detection of the extent thereof are carried out in a homogeneous solution. The reaction can be carried out utilizing a one stage or two stage incubation. A two stage incubation is preferably employed. Other approaches for detecting this oxidation reaction are measuring the rate of incorporation of tritium into D-arabinitol when the sample, NAD and [4(S)-$^3$H]NADH are incubated, or the separation and chromophoric detection of D-ribulose formed by oxidation of D-arabinitol.

In a heterogeneous assay approach, the reagents are as described above in the homogeneous approach. Generally, the D-arabinitol will be separated from the bulk of the sample, usually by a chromatographic method. The separated D-arabinitol will then be oxidized by use of a specific DADH and an NAD derivative and the product(s) detected as already described.

The assay will normally be carried out in an aqueous buffered medium at a moderate pH, generally that which provides optimum assay sensitivity. The assay can be performed either without separation (homogeneous) or with prior separation (heterogeneous) of any of the assay components or products.

It may be desirable or preferable to pretreat a sample to be assayed to remove interferents prior to conducting an assay. The sample can be subjected to, for example, ultrafiltration or elevated temperatures to accomplish this pretreatment. Samples include body fluids such as serum, whole blood, urine, etc.

The aqueous medium may be solely water or may include from 0.01 to 10 volume percent of a cosolvent. The pH for the medium will usually be in the range of about 5 to 11, more usually in the range of about 6 to 10.5, and preferably in the range of about 7 to 10. The pH value will usually be selected to maximize the extent and rate of oxidation of D-arabinitol without causing excessive decomposition of the DADH. Generally, the reaction will progress further toward completion as the pH is increased and as the cofactor concentration is increased.

Various buffers may be used to achieve the desired pH and maintain the pH during the determination. Illustrative buffers include glycine, phosphate, carbonate, tris, barbital and the like. The particular buffer employed is not critical to this invention, but in an individual assay one or another buffer may be preferred. Borate is not suitable for this assay.

Moderate temperatures are normally employed for carrying out the assay and usually constant temperatures during the period of the measurement. Incubation temperatures will normally range from about 50 to 45° C., more usually from about 150 to 40° C. Temperatures during measurements will generally range from about 100 to 50° C., more usually from about 150 to 40° C.

For detection of Candida infection the concentration of D-arabinitol that may be assayed will generally vary from below $1\times10^{-7}$ to $1\times10^{-3}$ M, more usually from about $1\times10^{-6}$ to $5\times10^{-4}$ M. In serum, the clinically relevant concentration will usually range from about $1\times10^{-6}$ to $1\times10^{-4}$ M. Considerations such as the sensitivity of "a" particular detection technique, the time desired to complete the assay, the cost of the reagents and the concentration of the D-arabinitol will normally determine the concentrations of the various reagents.

The concentration of the $NAD^+$ or a derivative thereof will affect the value and equilibrium of the reaction. Normally, in order to minimize the assay time, the $NAD^+$ concentration should be at least equal to the $K_m$ of the enzyme with respect to $NAD^+$. Further increasing the concentration of $NAD^+$, for example, to 10–100 $K_m$, is useful when low concentrations of D-arabinitol are present in order to assure maximal conversion to NADH. As for the enzyme, the greater the concentration of the enzyme the faster the reaction is completed. Usually it is desirable to use at least 0.1 IU, preferably at least 1 IU, more preferably at least 10 IU. However, the cost of this reagent may dictate the use of less than a most preferred concentration. The concentrations of reagents used to detect the NADH that is formed will depend on the particular detection method used, the required sensitivity of the method? and the potential for producing non-specific background signal with excess reagents.

While the order of addition may be varied widely, there may be certain preferences. The simplest order of addition is to add all the materials simultaneously and determine the signal produced. Alternatively, the reagents can be combined sequentially. As described above, one or more incubation steps may be involved subsequent to each addition, each generally ranging from about 10 seconds to 6 hours, more usually from about 30 seconds to 1 hour.

In a homogeneous assay after all of the reagents have been combined either simultaneously or sequentially, the presence of product produced as a result of the oxidation of D-arabinitol is determined. The presence and amount of such product is related to the amount of the D-arabinitol in the sample tested. The DADH enzyme of the invention is preferably first combined with the sample and enzyme cofactors. After incubation, either or both the chromophoric reagent and catalyst required to permit reaction of the NADH with the chromophoric reagent are added if not already included in the assay medium. The amount of chromophoric reagent employed is usually at least equimolar to the maximum amount of D-arabinitol that is expected in the assay medium, preferably at least 10 times the amount of D-arabinitol, more preferably at least 100 times the amount of D-arabinitol.

Another aspect of the present invention relates to kits useful for conveniently performing the assay method of the invention for determining the presence or amount of D-arabinitol in a sample suspected of containing the D-arabinitol. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. The kit comprises as one reagent a specific DADH enzyme in accordance with the invention. The kit can further comprise a cofactor such as $NAD^+$, and an agent that reacts with NADH to give a detectable product.

The kit can further include other separately packaged reagents for conducting an assay in accordance with this invention such as supports, ancillary reagents, sample pretreatment reagents, and so forth. A support can be a porous or non-porous water insoluble material. The support can be hydrophilic or capable of being rendered hydrophilic and includes inorganic powders, natural polymeric materials; synthetic or modified naturally occurring polymers, such as plastics; glass; ceramics; metals and the like.

Another embodiment in accordance with the present invention is directed to a composition comprising $NAD^+$ and a specific DADH enzyme capable of utilizing D-arabinitol as a substrate and substantially incapable of utilizing D-mannitol as a substrate.

Another embodiment of the present invention is a composition comprising an enzyme which is a dehydrogenase capable of catalyzing the oxidation of D-arabinitol at a rate of at least 10-fold faster than it catalyzes the oxidation of any other naturally occurring polyol, preferably at least 20-fold faster.

Another embodiment of the present invention is a composition comprising a DADH enzyme that binds to either or both of the monoclonal antibodies 3D6 and 5E11 with an affinity constant of at least $1\times10^6 M^{-1}$, preferably at least $1\times10^8 M^-$. Another embodiment of the present invention is a C. shehatae enzyme that binds either or both of the monoclonal antibodies 3D6 and 5E11. Another embodiment of the present invention is DADH from C. tropicalis that also binds either or both of the monoclonal antibodies 3D6 and 5E11.

EXAMPLES

The invention is further demonstrated by the following illustrative examples. Parts and percentages used herein are by weight unless otherwise indicated. Temperatures are in degrees centigrade (° C.).

Example 1

Purification of D-Arabinitol Dehydrogenase From Candida Tropicalis

Centrifugation and other protein purification steps were performed at 4° unless otherwise noted. Four liters of cells were grown in Yeast Nitrogen Base (Difco) supplemented with 0.5% (w/v) D-arabinitol on a gyrotary shaker at room temperature. The cells were harvested by centrifugation after they reached late log phase in their growth cycle ($OD_{660}$>5.0). The cells were then washed with distilled water, repelleted and the wet weight of the cell pellets was determined. The pellets were resuspended in 0.1 M $NaH_2PO_4$, $10^{-7}$ M pepstatin A, 1 mM phenylmethylsulfonyl fluoride, pH 7.0 with NaOH at room temperature, using two mls of the above buffer per gram of wet weight cells. Acid-washed glass beads (0.45–0.55 mm) were added to the resuspended pellets using two grams of beads for each gram of wet weight cells. The cells were then disrupted in a Braun MSK Cell Homogenizer for 5 min while being cooled with liquid nitrogen. The disrupted cells were removed from the glass beads and were spun at 5,000×g for 5 min to pellet cell wall material. The supernatant was removed and spun at 100,000×g at 4° for 1 hr in an ultracentrifuge. The resulting supernatant was removed and its volume and protein concentration was determined. For every gram of protein, 90 mg of protamine sulfate was added dropwise from a 2% (w/v) stock over 5 min while stirring on ice. After equilibrating the solution by stirring for an additional 15 min on ice, the nucleic acid-protein precipitate was removed by centrifugation at 30,000×g for 15 min. The resulting supernatant was brought to 40% saturation with ammonium sulfate crystals, which were added over a period of 20 min while stirring the solution on ice. After equilibrating the solution by stirring for an additional 30 min on ice, the protein precipitate was recovered by spinning the solution at 100,000×g for 15 min. The resulting pellet was resuspended in running buffer (50 mM $NaH_2PO_4$, 0.5 M NaCl, 5 MM $MgCl_2$, $10^{-7}$ M pepstatin A, pH 7.0 with NaOH at room temperature) using 1/20th the volume of the 100,000×g supernatant. The protein solution was then loaded on a reactive yellow 86 dye ligand column (1 cm×3.5 cm) and the column was washed with 5 column volumes of running buffer. It should be noted that other dye ligand columns can be used in this step of the procedure, when lesser purification factor can be tolerated. Such dye ligands include by way of illustration and not limitation reactive blue 4, reactive red 120, reactive blue 2, reactive green 5, reactive blue 72, and reactive yellow 3. The D-arabinitol dehydrogenase was eluted by washing the column with 3 column volumes of running buffer supplemented with 1 mM NADH. The eluted protein was concentrated using a Centricon 30 microconcentrator device (Amicon) to a final concentration of at least 1 mg/ml. The D-arabinitol dehydrogenase was stored at −80° C. The average yield of D-arabinitol dehydrogenase was 1.0–1.5 mg while purity was greater than 90% as judged by sodium dodecylsulfate (SDS)-polyacrylamide gel electrophoresis. Table 1 summarizes the protein purification results.

subcutaneous injection. The immunogen was prepared by diluting purified D-arabinitol dehydrogenase from *Candida tropicalis* (see Example 1) into Hanks Balanced Saline Solution (HBSS) at a concentration of 500 µg/2.0 ml. The antigen was then added to an adjuvant mixture of monophosphoryl lipid A and trehalose dimycolate in 2% squalene (RIBI Immunochemical Research Inc.) and used for injections. Mice were boosted twice with 50 µg of immunogen. A final intravenous injection of 200 µg *C. tropicalis* D-arabinitol dehydrogenase in HBSS was performed prior to fusion.

C. Cell Fusion

Spleen cells were harvested from the immunized mice and fused with P3×63-AG8.653 myeloma cells (ATCC #CRL 1580) using polyethylene glycol. The cells were resuspended in HAT (0.1 mM hypoxanthine, 0.016 mM thymidine and 0.4 µM aminopterin, Sigma) supplemented media and distributed into 96-well microtiter plates. Four days later cells were fed by replacing half the HAT supplemented media.

D. Hybridoma Screening

Hybridomas were screened for antibodies specific for *C. tropicalis* D-arabinitol dehydrogenase by a reverse ELISA method. Microtiter EIA plates (Costar #3595) were coated with rabbit anti-mouse IGA, A, M, heavy and light chains (Zymed) at a 1:100 dilution in PBS (0.01 M $NaHPO_4$, 0.01 M $NaH_2PO_4$, 0.015 M NaCl, 0.001% $NaN_3$, adjusted to pH 7.2). 100 µl of the above solution was added per well and incubated either at 37° for at least one hour or at 4° overnight. Any unbound sites on the plate were blocked with 1% (v/v) normal sheep serum (NSS, Sigma) in PBS (200 µl/well). After blotting off the NSS, 50 ul of hybridoma culture supernatant was added per well. The plates were

TABLE 1

C. TROPICALIS ATCC 750
PROTEIN PURIFICATION TABLE

| SAMPLE | VOLUME (ml) | TOTAL PROTEIN (mg) | TOTAL ACTIVITY* (µmoles NADH formed per min) | SPECIFIC ACTIVITY (Activity per mg protein) | PURIFICATION FACTOR (P.F.) | YIELD (%) |
|---|---|---|---|---|---|---|
| 100,000 × g | 55 | 1661 | 422.4 | 0.254 | 1.00 | 100 |
| Protamine SO4 | 60 | 1888 | 446.4 | 0.236 | 0.93 | 100 |
| $(NH_4)_2SO4$ | 3 | 110.7 | 225.6 | 2.038 | 8.62 | 53.4 |
| Y-86 Column | 0.162 | 1.2 | 243.7 | 203.0 | 99.62 overall P.F. 799.2 | 58.0 |

*Activity was determined in 1 ml of 1.5 mM NAD, 50 mM D-arabinitol in 50 mM 3-(cyclohexylamino)-2-hydroxy-1-propanesulfonic acid (CAPSO), pH 9.5, 100 mM NaCl, 5 mM $MgCl_2$ at 25° C. The production of NADH was monitored by Example 2

Preparation of Monoclonal Antibodies Against *Candida Tropicalis* D-Arabinitol Dehydrogenase A. General Methods The standard hybridoma procedures used have been described in detail (Kohler, G.; Milstein, C. *Nature* 1975, 256, 495–7; Hurrell, J. G. R. "Monoclonal Hybridoma Antibodies: Techniques and Applications", CRC Press, 1982, Boca Raton, Fla. 33431).

B. Immunization

Balb/C mice (Charles River Laboratories) were immunized with 50 µg of immunogen by either intraperitonial or incubated at 250 for one hour. The plates were then washed four times with ELISA Wash Buffer (0.05% (v/v) Tween-20 in PBS). Excess wash buffer was blotted from the plate and a 2 ug/ml solution of D-arabinitol dehydrogenase in PBT (0.2% (w/v) bovine serum albumin and 0.1% (v/v) Tween-20 in PBS) was added to the plate at 100 µl/well. The EIA plate was incubated for one hour at 250. The plates were then washed four times with ELISA Wash Buffer and excess buffer was blotted from the plate. The plates were then developed with a substrate solution containing 50 mM D-arabinitol (Aldrich) and 1.5 mM $NAD^+$ in 50 mM CAPSO, 100 mM NaCl, 5 mM $MgCl_2$ adjusted to pH 9.5. The plates were incubated at 370 for 30 minutes and the NADH product was measured at 340 nm. Alternatively, the production of NADH was coupled with the reduction of p-iodonitrotetrazolium violet (INT, Sigma) through the enzyme diaphorase (Sigma). Diaphorase (0.534 IU/ml, final concentration) and INT (0.074 mM, final concentration) were added to the above reaction mixture. The reaction was incubated as above and the production of reduced INT was monitored at 492 nm. Wells with readings at least three times higher than the background were considered positives. Cells from ELISA positive wells were subcloned until stable monoclonal antibody secretion was achieved. During the subcloning, ELISA screens were also done substituting *C. shehatae* D-arabinitol dehydrogenase for the *C. tropicalis* enzyme.

E. Antibody Production in Ascites

To scale up monoclonal antibody production in ascites, mice were primed by an intraperitoneal injection of Incomplete Freund's Adjuvant to facilitate tumor growth 2 to 7 days prior to passage of cells. Cells were grown up in a T-75 flask, to a final density of about $18 \times 10^6$ cells in 50 ml, centrifuged, and then resuspended in 2 mL of Dulbecco's Modified Eagle Medium (Gibco) with 10% FBS, 10% NCTC-135 (Gibco), 1 mM oxaloacetic acid (Sigma), 1 mM sodium pyruvate (Gibco), 4 mM L-glutamine (Sigma), 50 ug/mL gentamicin (Gibco), 10 $\mu$g/mL insulin (Sigma), 20 mM Hepes (Sigma). Each mouse received a 0.5 mL intraperitoneal injection of approximately $4–5 \times 10^6$ cells. Ascites tumors usually developed within a week or two. The ascites fluid containing a high concentration of antibody was drained from the peritoneal cavity using a hypodermic needle. The fluid was allowed to clot at room temperature and then centrifuged at 1500 rpm in a Beckman Model TJ-6 Centrifuge for 30 minutes. The antibody containing fluid was poured off and stored at 4°.

Example 3

Elisa Binding of Monoclonal Antibodies to Different D-Arabinitol Dehydrogenases

Monoclonal antibodies produced against *C. tropicalis* D-arabinitol dehydrogenase were screened for binding to D-arabinitol specific dehydrogenases purified from *C. tropicalis* and from *C. shehatae* by the reverse ELISA method described above. These monoclonal antibodies were also screened for binding to polyol dehydrogenases that could utilize other sugar alcohol substrates in addition to D-arabinitol. A *C. shehatae* polyol dehydrogenase that could utilize D-arabinitol, D-sorbitol, xylitol and D-mannitol was tested. Also tested was D-arabinitol dehydrogenase from *Aerobacter aerogenes*, an enzyme that uses either D-arabinitol or D-mannitol as a substrate.

The D-arabinitol dehydrogenase from *C. tropicalis* was purified as described in Example 1. The purification of D-arabinitol dehydrogenase from *C. shehatae* was similar to the purification of D-arabinitol dehydrogenase from *C. tropicalis* with some exceptions. The cells disrupted in a Braun MSK Cell Homogenizer were removed from the glass beads and spun at 30,000×g for 15 minutes to pellet cell wall material. In addition, 60% saturation with ammonium sulfate was used instead of 40%, to precipitate the protein. This allowed the precipitation of both the D-arabinitol dehydrogenase and the polyol dehydrogenase. The D-arabinitol dehydrogenase was purified over a reactive yellow 86 dye ligand column as described in Example 1. The polyol dehydrogenase from this same strain was purified by running the flowthrough from the reactive yellow 86 dye ligand column through a reactive blue 2 dye ligand column (1.0 cm×6.0 cm). The polyol dehydrogenase was then eluted by washing the column with 3 column volumes of running buffer supplemented with 10 mM NAD. D-arabinitol dehydrogenase from *Aerobacter aerogenes* (lyophilized cells, Type 1, Sigma) was purified as described in Neuberger, et al., in *Biochem. J.*, 183 (1979) 31–42.

The reverse ELISA screening was as above except a 1:100 dilution of ascites in PBT (100 $\mu$L/well) was used instead of culture supernatant. In addition, the purified D-arabinitol dehydrogenases from each strain were diluted to 0.2 IU/mL (where an international unit is the amount of NADH produced/min). As a control, the D-arabinitol dehydrogenase activity was confirmed for each activity assay as follows: 10 gL of unbound D-arabinitol was removed from ELISA wells and enzyme activity was checked with the developing reagents as described above. For a negative antibody control, *Chlamydia trachomatis*-immunized mouse sera diluted 1:100 in PBT was used.

Results are summarized in Table 2. Each monoclonal antibody was analyzed in duplicate (DUP) with each of the four enzymes. Blanks were run by repeating the above experiments in the absence of the monoclonal antibodies and blank readings were subtracted from the DUP values. The average of the DUP values is presented in Table 2. The results show that the monoclonal antibodies produced against *C. tropicalis* D-arabinitol dehydrogenase bind the D-arabinitol-specific dehydrogenases from both *C. tropicalis* and *C. shehatae*, as evidenced by ELISA readings that are elevated relative to those observed with the Chlamydia antibody. In contrast, relatively little, if any, binding is seen with the polyol dehydrogenases purified from *C. shehatae* and from *A. aerogenes* as evidenced by the fact that these readings are not significantly higher than those observed with the Chlamydia antibody. These results demonstrate that the monoclonal antibodies bind only D-arabinitol specific dehydrogenases and do not bind to less specific dehydrogenases that utilize either D-arabinitol or other sugar alcohols as substrates.

TABLE 2

ELISA BINDING OF POLYOL DEHYDROGENASES TO MONOCLONAL ANTIBODIES SPECIFIC FOR *C. TROPICALIS* D-ARABINITOL DEHYDROGENASE

| Antibody | CTDADH[1] | CSDADH[2] | CSPDH[3] | AADADH[4] |
| --- | --- | --- | --- | --- |
| 3D6 | 0.201 | 0.146 | 0.009 | 0.004 |
| 5E11 | 0.237 | 0.169 | 0.008 | 0.004 |
| 1B9 | 0.171 | 0.049 | 0.007 | 0.003 |
| 5F3 | 0.186 | 0.079 | 0.006 | 0.002 |
| 6B3 | 0.265 | 0.060 | 0.004 | −0.002 |
| 1H4 | 0.337 | 0.043 | −0.002 | −0.001 |
| chlamydia | 0.007 | 0.005 | 0.003 | 0.010 |

1CTDADH = *C. tropicalis* D-arabinitol dehydrogenase
2CSPADH = *C. shehatae* D-arabinitol dehydrogenase
3CSPDH = *C. shehatae* polyol dehydrogenase
4AADADH = *A. aerogenes* D-arabinitol dehydrogenase Example 4

A Fluorogenic Assay For D-Arabinitol in Human Serum

Fluorogenic Assay Protocol

Human serum was diluted 1:3 (v/v) with 10 mmol/L citrate (pH 4.0), placed in a boiling water bath for 10 min, and then centrifuged at 10,000×g for 10 min to remove precipitated material. The supernatant was used as the sample. Reaction mixtures (vol.=0.4 mL) contained 0.3 mL of sample, 1 mmol/L NAD$^+$, 4 mmol/L Mg$^{2+}$, 0.35 IU *C. tropicalis* D-arabinitol dehydrogenase prepared as described in Example 1, and 0.1 mol/L Tris (pH 9.5). Incubation was for 15 min at room temperature to promote the D-arabinitol dehydrogenase-catalyzed oxidation of D-arabinitol with concomitant reduction of NAD$^+$ to NADH. This initial incubation stage was terminated by reducing the pH of the reaction mixture to 5.8 with 0.03 mL 1.0 mol/L citrate (pH 3.6). Resazurin (12.5 μmol/L) and diaphorase (0.15 IU) were then added, and the sample was reincubated at room temperature to promote the diaphorase-catalyzed utilization of NADH (which had accumulated in the initial incubation stage) for the reduction of resazurin to resorufin. Formation of the latter was monitored fluorometrically (Excitation=560 nm, Emission=580 nm) using a Perkin-Elmer fluorescence spectrophotometer, Model #650-40, and was complete within 30 sec.

Calibration Curve for the Fluorogenic Assay

Results from a series of assays of a pool of normal human serum into which varying amounts of D-arabinitol had been added are summarized in Table 3. A plot of fluorescence emission at 580 nm (Y-axis) vs. amount of D-arabinitol added (X-axis) yields the calibration curve for the assay. The absolute value of the x-intercept of this plot is a measure of the endogenous level of D-arabinitol present in the serum pool. In 22 replicate experiments, the calibration curves were linear (mean $r^2=0.998$) and the observed D-arabinitol concentrations in supplemented samples differed from the expected amounts (y-intercept+amount added) by no more than 0.6 μmol/L or 13.2%.

The results of quadruplicate analyses of a pool of normal human serum into which 0, 2, 7 and 14 μmol/L D-arabinitol had been added are illustrated in Table 4. The mean measured D-arabinitol concentrations were within either 0.58 μmol/L or 6.9% of the expected amounts (amount added plus measured D-arabinitol concentration of the unspiked pool), and the standard deviations were no more than 0.60 μmol/L or 5.9%.

Accuracy of the Fluorogenic D-Arabinitol Assay

The results of analyses of several individual human sera into which various amounts of D-arabinitol had been added are illustrated in Table 5. For each serum, the D-arabinitol concentration determined in the supplemented sample was divided by the sum of the concentration determined in the unsupplemented sample plus the amount contained in the supplement to yield a measure of the accuracy of the assay. In all instances, measured D-arabinitol concentrations were within 16% of the expected amounts. The mean±SD endogenous D-arabinitol concentration in the 11 normal adult sera was found to be 1.86±0.36 μmol/L.

Specificity of the Fluorogenic Assay

A series of sugars and sugar alcohols normally present in human serum were assessed for reactivity in the fluorometric assay. The results are summarized in Table 6. Of the compounds examined, significant reactivity relative to that observed with an equimolar concentration of D-arabinitol was found only with xylitol (3.3%). D-glucose at concentrations as great as 5.0 mmol/L was not utilized as "aa" substrate.

TABLE 3

CALIBRATION CURVE FOR THE FLUOROGENIC D-ARABINITOL ASSAY

| D-Arabinitol Added (μmol/L) | Fluorescence Emission, 580 nm (Units) |
|---|---|
| 0 | 19.6 |
| 4 | 50.5 |
| 182 | 78.7 |
| 16 | 141 | y = 19.500 + 7.5825x
$r^2$ = 1.000

TABLE 4

ACCURACY AND PRECISION OF SERUM D-ARABINITOL DETERMINED WITH THE FLUOROGENIC ASSAY

| D-Arabinitol Added (μmol/L) | Observed[a] [D-Arabinitol] (μmol/L) | CV(%) | Observed/ Expected[b] |
|---|---|---|---|
| 0 | 1.45 ± 0.086 | 5.9 | — |
| 2 | 3.43 ± 0.096 | 2.8 | 0.99 |
| 7 | 7.83 ± 0.37 | 4.7 | 0.93 |
| 14 | 15.4 ± 0.60 | 3.9 | 1.00 |

[a]Mean ± standard deviation of quadruplicate analyses.
[b]Observed mean [D-arabinitol]/(D-arabinitol added + 1.45 μmol/L.)

TABLE 5

ACCURACY OF THE FLUOROGENIC D-ARABINITOL ASSAY IN SEVERAL NORMAL HUMAN SERA

| Human Serum No. | D-Arabinitol Added (μmol/L) | Observed [D-Arabinitol] (μmol/L) Unsupple- mented Sample | Observed [D-Arabinitol] (μmol/L) Supple- mented Sample | Observed/ Expected[a] |
|---|---|---|---|---|
| 1 | 2 | 1.76 | 3.94 | 1.05 |
| 2 | 1.5 | 1.94 | 3.24 | 0.94 |
| 3 | 3 | 1.96 | 4.56 | 0.92 |
| 4 | 10 | 1.96 | 10.7 | 0.89 |
| 5 | 75 | 1.75 | 85.7 | 1.12 |
| 6 | 7 | 2.04 | 8.3 | 0.92 |
| 7 | 8 | 1.85 | 10.0 | 1.02 |
| 8 | 40 | 1.75 | 48.0 | 1.15 |
| 9 | 1 | 2.55 | 3.57 | 1.01. |
| 10 | 8 | 1.57 | 9.91 | 1.04 |
| 11 | 2 | 1.33 | 2.80 | 0.84 |
| 11 | 5 | 1.33 | 5.48 | 0.87 |
| 11 | 10 | 1.33 | 9.99 | 0.88 |
| 11 | 45 | 1.33 | 44.7 | 0.96 |

[a]Observed [D-arabinitol] in supplemented sample/(D-arabinitol added + observed [D-arabinitol] in unsupplemented sample).

TABLE 6

SPECIFICITY OF THE FLUOROGENIC D-ARABINITOL ASSAY

| Compound Added | Concentration (μmol/L) | Relative Reactivity (%) |
|---|---|---|
| D-arabinitol | 5 | 100 |
| L-arabinitol | 5 | 0 |
| ribitol | 5 | 0 |
| xylitol | 5 | 3.3 |
| D-sorbitol | 5 | 0.1 |

TABLE 6-continued

SPECIFICITY OF THE FLUOROGENIC D-ARABINITOL ASSAY

| Compound Added | Concentration (μmol/L) | Relative Reactivity (%) |
|---|---|---|
| D-mannitol | 5 | 0 |
| erythritol | 5 | 0 |
| threitol | 5 | 0.1 |
| galactitol | 5 | 0.6 |
| D-fructose | 500 | 0 |
| D-galactose | 500 | 0.9 |
| D-mannose | 500 | 0.3 |
| D-glucose | 5000 | 0 |

Assays were performed as described in Example 4 except the sample contained, instead of the boiled serum supernatant, the indicated compound in PBS/10 mmol/L citrate, pH 4.0 (1:3,v/v).

Example 5

A Radioisotopic Exchange Assay For D-Arabinitol in Human Serum

Tritium Exchange Assay Protocol

Assay incubation solutions (vol.=0.1 mL) contained 0.05 mL ultrafiltered human serum, 0.2 mmol/L unlabeled $NAD^+$, 0.015 mmol/L (0.62 Ci/mmol) [4(S)-$^3$H]NADH, 2 mg/mL BSA, 0.2 mmol/L DTT, 4 mmol/L $Mg^{2+}$, 40 mmol/L Tris (pH 9.2), and 0.35 IU C. tropicalis D-arabinitol dehydrogenase. Incubation was for 2 hr. at room temperature to promote the D-arabinitol dehydrogenase-catalyzed exchange of tritium from [4(S)-$^3$H]NADH into D-arabinitol. After incubation, the sample was diluted with 0.9 mL distilled water and applied to a 2 mL column of AG 2-X8 (Bio Rad, Cat. No. 731-6247) preequilibrated in the OH form. The column was eluted with 6 mL distilled water and the eluate was collected, diluted 1:1 (v/v) with 250 mmol/L $NH_4OAc$ (pH 8.8), and applied to a 1 mL column of phenylboronate (Pierce, Cat. No. 20368) preequilibrated with the $NH_4OAc$ buffer. The column was washed with 10 mL 250 mmol/L $NH_4OAc$ (pH 8.8) and subsequently eluted with 4 mL 0.1 formic acid. The formic acid eluate was analyzed for tritium by scintillation spectrometry.

Calibration Curve For the Tritium Exchange Assay

Results from a series of assays of a pool of normal human serum into which various amounts of D-arabinitol had been added are illustrated in Table 7. A plot of tritium recovered (Y-axis) vs. the amount of D-arabinitol added (X-axis) yields the calibration curve for the assay. The absolute value of the X-intercept of the curve is a measure of the sum of endogenous D-arabinitol and D-ribulose present in the serum pool. The endogenous serum concentration of D-ribulose can be obtained by carrying out the assay under similar conditions but in the absence of $NAD^+$ and determining tritium incorporation into D-arabinitol. The calibration curve is linear ($r^2$=0.990) and the observed D-arabinitol concentrations in supplemented samples differed from the expected amounts (endogenous+amount added) by no more than 0.42 μmol/L or 7.9%.

TABLE 7

CALIBRATION CURVE FOR THE TRITIUM EXCHANGE ASSAY

| Assay No. | D-Arabinitol Added (μmol/L) | Tritium Recovered (cpm × 0.001) |
|---|---|---|
| 1 | 0 | 25.5 |
| 2 | 2 | 45.3 |
| 3 | 4 | 62.8 |
| 4 | 6 | 72.9 |
| 5 | 8 | 90.8 |

$y = 27.82 + 7.91x$
$r^2 = 0.990$

Example 6

An Automated Chromogenic Assay For D-Arabinitol in Human Serum

Automated Chromogenic Assay Protocol

Assays were performed on the COBAS-MIRA (Hoffmann LaRoche). Samples were human sera pretreated by boiling as indicated in the fluorometric assay protocol. In addition to a diluent (1 mol/L glycine, pH 10.5), the following three reagents were employed:

1. Enzyme Reagent (10 mmol/L Tris/Acetate (pH 6.0), 100 mmol/L NaCl, 10 mmol/L $Mg^{2+}$, 2.33 mmol/L $NAD^+$, 20 μg/mL BSA, and 3.5 IU/mL C. tropicalis D-arabinitol dehydrogenase).
2. Coupling Reagent (3.18 mmol/L iodonitrotetrazolium (INT), 66.7 mmol/L EDTA (pH 9.0) and 0.03% Pluronic 25R2).
3. Diaphorase Reagent (60 U/mL C. kluyveri diaphorase (Sigma, Cat. No. 02381) in PBS).

With a cycle time of 25 seconds and an assay incubation temperature of 30° C., the following assay steps are carried out by the MIRA:

Cycle 1 mix sample (vol.=85+10 μL diluent)+enzyme reagent (vol.=100 μL).

Cycle 37 add coupling reagent (vol.=15+5 μL dd$H_2O$)

Cycle 38 read $Abs_{500\ nm}$

Cycle 39 add diaphorase reagent (vol.=3+5 μL dd$H_2O$)

Cycle 40 read $Abs_{500\ nm}$

The assay result is reported as ΔA=A500 nm, cycle 40—A500 nm, cycle 38.

Calibration Curve for the Automated Chromogenic Assay

Results from a series of assays of a pool of normal human serum into which various amounts of D-arabinitol had been added are illustrated in Table 8. The endogenous level of D-arabinitol in this serum pool was previously determined to be 1.0 μmol/L by the enzymatic method of Wong and Brauer (J. Clin. Microbiol. 26, 1670 (1988). A plot of mean $AAbs_{500\ nm}$ (Y-axis) vs. total serum D-arabinitol (endogenous+amount added) (X-axis) yields the calibration curve for the assay. The calibration curve is linear ($r^2$=1.00) and the observed D-arabinitol concentrations in supplemented samples differed from the expected amounts (endogenous+amount added) by no more than 0.17 μmol/L or 1.0%.

TABLE 8

CALIBRATION CURVE FOR THE AUTOMATED CHROMOGENIC ASSAY

| Assay No. | Serum D-Arabinitol ($\mu$mol/L) | Mean $\Delta Abs_{500\ nm}$ (x $10^3$) |
|---|---|---|
| 1 | 1.0 | 9.4 |
| 2 | 6 | 16.5 |
| 3 | 11 | 23.65 |
| 4 | 16 | 31.35 |
| 5 | 21 | 38.45 |
| 6 | 26 | 45.45 |

$y = 7.89 + 1.45\ x$
$r^2 = 1.00$

The cell lines designated DADH 1-5E11 and DADH 1-3D6, were deposited on June 18, 1991 with the American Type Culture Collection (ATCC), located at 12301 Parklawn Drive, Rockville, Md. 28852, U.S.A., and received ATCC designations HB 10776 and HB 10777, respectively.

Although the foregoing invention has been described in some detail by way of illustration and example for purposes of clarity and understanding, it will be obvious that certain changes or modifications may be practiced within the scope of the appended claims.

What is claimed is:

1. A D-arabinitol dehydrogenase enzyme in purified form capable of catalyzing the oxidation of D-arabinitol and substantially incapable of catalyzing the oxidation of D-mannitol and that is substantially free of other enzymes capable of oxidizing D-mannitol.

2. The enzyme of claim 1 which is obtained from an organism of the genus Candida.

3. The enzyme of claim 1 which is obtained from the organism *Candida tropicalis.*

4. The enzyme of claim 1 which is obtained from the organism *Candida shehatae.*

5. A D-arabinitol dehydrogenase enzyme in purified form capable of binding to at least one of the monoclonal antibodies selected from the group consisting of 3D6 and 5E11, said enzyme being substantially free of other enzymes capable of oxidizing D-mannitol.

6. The enzyme of claim 5 wherein said enzyme is capable of binding to both of said antibodies with binding constants of at least $10^6\ M^{-1}$.

7. An enzyme in purified form specific for the oxidation of D-arabinitol wherein said enzyme is substantially incapable of catalyzing the oxidation of D-mannitol and is substantially free of other enzymes capable of oxidizing D-mannitol.

* * * * *